US009679552B2

(12) United States Patent
Ganeshkumar et al.

(10) Patent No.: US 9,679,552 B2
(45) **Date of Patent: *Jun. 13, 2017**

(54) ACTIVE REDUCTION OF HARMONIC NOISE FROM MULTIPLE NOISE SOURCES

(71) Applicant: Bose Corporation, Framingham, MA (US)

(72) Inventors: Alaganandan Ganeshkumar, North Attleboro, MA (US); Dennis D. Klug, West Bloomfield, MI (US)

(73) Assignee: Bose Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/098,863

(22) Filed: Apr. 14, 2016

(65) Prior Publication Data

US 2016/0225364 A1 Aug. 4, 2016

Related U.S. Application Data

(63) Continuation of application No. 14/494,852, filed on Sep. 24, 2014, now Pat. No. 9,344,796, which is a (Continued)

(51) Int. Cl.

*A61F 11/06* (2006.01)
*G10K 11/178* (2006.01)
*H04R 3/00* (2006.01)

(52) U.S. Cl.

CPC .......... *G10K 11/178* (2013.01); *H04R 3/002* (2013.01); *G10K 2210/1282* (2013.01); (Continued)

(58) Field of Classification Search

CPC .............................. G10K 11/178; H04R 3/002
See application file for complete search history.

(56) References Cited

U.S. PATENT DOCUMENTS 5,170,433 A 12/1992 Elliott et al.
5,410,606 A 4/1995 Imai et al.
(Continued)

FOREIGN PATENT DOCUMENTS

JP H06-109067 A 4/1994
JP H07-28474 A 1/1995
(Continued)

OTHER PUBLICATIONS

International Search Report and Written Opinion dated Jun. 5, 2014 for PCT/US14/19354.

(Continued)

*Primary Examiner* — Simon King
(74) *Attorney, Agent, or Firm* — Bose Corporation

(57) ABSTRACT

A system and method for reducing harmonic noise caused by two or more noise sources by causing one or more loudspeakers to produce sounds that are at about the same frequencies as the noise and of substantially opposite phase. There is a noise canceller associated with each noise source. Each noise canceller includes a harmonic sine wave generator that generates an output sine wave. Each noise canceller also has an adaptive filter that uses a sine wave to create a noise reduction signal that is used to drive one or more transducers with their outputs directed to reduce noise caused by the noise sources. There is an overlap detector that compares the harmonic frequencies and, based on their proximity, alters the operation of one or more adaptive filters.

18 Claims, 3 Drawing Sheets

Related U.S. Application Data continuation-in-part of application No. 13/849,856, filed on Mar. 25, 2013, now Pat. No. 9,191,739.

(52) U.S. Cl.
CPC ................ *G10K 2210/3028* (2013.01); *G10K 2210/3032* (2013.01); *G10K 2210/3054* (2013.01); *H04R 2499/13* (2013.01)

(56) References Cited

U.S. PATENT DOCUMENTS

| | | | | |
|---|---|---|---|---|
| 5,416,844 | A * | 5/1995 | Nakaji | G10K 11/1784 381/71.4 |
| 8,194,873 | B2 | 6/2012 | Pan et al. | |
| 8,204,242 | B2 | 6/2012 | Pan et al. | |
| 8,306,240 | B2 | 11/2012 | Pan et al. | |
| 8,355,512 | B2 | 1/2013 | Pan et al. | |
| 2004/0247137 | A1 | 12/2004 | Inoue et al. | |
| 2005/0207585 | A1 | 9/2005 | Christoph | |
| 2007/0140503 | A1 | 6/2007 | Sakamoto et al. | |
| 2008/0292110 | A1 | 11/2008 | Kobayashi et al. | |
| 2009/0060217 | A1* | 3/2009 | Sakamoto | G10K 11/178 381/71.4 |
| 2009/0175461 | A1* | 7/2009 | Nakamura | G10K 11/1788 381/71.1 |
| 2010/0098263 | A1* | 4/2010 | Pan | G10K 11/178 381/71.11 |
| 2010/0098265 | A1* | 4/2010 | Pan | G10K 11/178 381/94.1 |
| 2010/0111318 | A1* | 5/2010 | Nakamura | G10K 11/1782 381/71.8 |
| 2011/0021691 | A1 | 1/2011 | Chiang | |
| 2011/0235693 | A1* | 9/2011 | Lee | H04S 7/00 375/224 |
| 2012/0057720 | A1* | 3/2012 | Van Leest | G10K 11/1782 381/71.11 |

FOREIGN PATENT DOCUMENTS

| | | | |
|---|---|---|---|
| JP | H07-104767 | A | 4/1995 |
| JP | 2009-298289 | A | 12/2009 |
| JP | 2016-505466 | A | 10/2011 |

OTHER PUBLICATIONS

International Preliminary Report on Patentability dated Sep. 29, 2015 for PCT/US14/19354.

JP office action dated Nov. 15, 2016 for JP 2016-505466.

* cited by examiner

ACTIVE REDUCTION OF HARMONIC NOISE FROM MULTIPLE NOISE SOURCES

CROSS-REFERENCE TO RELATED APPLICATIONS

This application is a continuation of U.S. application Ser. No. 14/494,852, filed Sep. 24, 2014, which is a continuation-in-part of U.S. application Ser. No. 13/849,856, filed Mar. 25, 2013, now a granted U.S. Pat. No. 9,191,739, the contents of which are incorporated herein by reference.

FIELD

This disclosure relates to the active reduction of harmonic noise from two or more noise sources.

BACKGROUND

Engine harmonic cancellation systems are adaptive feed-forward noise reduction systems that are used in motor vehicles, for example in cabins or in muffler assemblies, to reduce or cancel engine harmonic noise. A sine wave at the frequency to be cancelled is used as an input to an adaptive filter. Engine harmonic cancellation systems also use one or more microphones as error input transducers. The adaptive filter can alter the magnitude and/or the phase of the input sine wave. The output of the adaptive filter is applied to one or more transducers that produce sound (i.e., loudspeakers) that is acoustically opposite to the undesirable engine harmonics that are to be canceled. The aim of the system is to cancel the noise at the frequency or frequencies of interest by adaptively minimizing the total energy across all error microphone input signals. In order to do so, the loudspeaker outputs have a negative gain.

Harmonic noise cancellation systems are also used to cancel or reduce noise caused by noise sources other than engines. One additional source of noise in motor vehicles is the propeller shaft, also known as the drive shaft. Because geared transmissions are used to transfer engine rotation to propeller shaft rotation, the propeller shaft rotation rate is not fixed relative to the engine rotation rate. The engine and propeller shaft thus can be sources of noise in a vehicle cabin at different frequencies.

In order to cancel noise from both an engine and a propeller shaft, a noise reduction system requires two feed-forward adaptive filters. When the two frequencies being cancelled are coincident or close, the stability margins of the filters can be compromised. This increases the possibility of divergence of the filter algorithms, which can lead to the creation of loud and noticeable noise artifacts.

SUMMARY

The system and method of this disclosure are effective to reduce the audible artifacts that can be created by an adaptive feed-forward noise reduction system when two or more frequencies being cancelled are too close to each other. In one example, the frequencies being cancelled can include a fixed frequency, engine harmonic and propshaft harmonic that are targeting nearby frequencies. In another example, the frequencies being cancelled include multiple engine harmonics (e.g., at low engine speeds where the harmonics are closer in frequency). In yet another example, the system and method may be configured for cancelling frequencies from four or more sources and the frequencies can include, inter alia, fixed frequency, engine harmonic, propshaft harmonic, tire harmonic, vehicle electric motor. The reduction of audible artifacts can be accomplished by determining the proximity of the frequencies being cancelled and based on the proximity altering the operation of one or more of the adaptive filters.

All examples and features mentioned below can be combined in any technically possible way.

In one aspect, a system for reducing harmonic noise caused by a plurality of noise sources by causing one or more loudspeakers to produce sounds that are at about the same frequencies as the noise and of substantially opposite phase, includes a plurality of noise cancellers, each noise canceller comprising a harmonic sine wave generator that generates an output sine wave having a frequency that corresponds to the noise to be reduced, and an adaptive filter that uses a sine wave to create a noise reduction signal that is used to drive one or more transducers with their outputs directed to reduce noise caused by the noise sources. There is also an overlap detector that compares the frequencies and, based on the proximity of the frequencies, alters the operation of one or more of the adaptive filters.

Embodiments may include one of the following features, or any combination thereof. The overlap detector may alter the operation of one or more of the adaptive filters by changing the values of one or more variable parameters (e.g., adaptation step size and/or leakage parameter) of an adaptive filter; the variable parameters can include the adaptation step sizes of the adaptive filters, where the step sizes are decreased when the proximities of the frequencies are close. For example, the adaptation step size may be decreased by about one-half when two input signal frequencies are approximately coincident. The system can also include a computer memory that stores relationships between the proximity of the frequencies and the resulting changes in the values of the adaptive filter parameters. The transducer outputs may be directed into the cabin of a motor vehicle. At least one of the noise sources can include a rotating device. The noise sources can be the vehicle engine and the vehicle propeller shaft. At least one of the noise cancellers can be configured to create a noise reduction signal that is used to drive one or more transducers with their outputs directed to reduce noise at a fixed frequency. In some cases, at least one of the harmonic sine wave generators is configured to generate an output sine wave based on a fixed frequency value received from computer memory. At least one of the noise cancellers can include a harmonic frequency computer that computes from an input signal a harmonic frequency and provides the harmonic frequency to a corresponding one of the harmonic sine wave generators. At least one of the noise cancellers can be configured to create a noise reduction signal that is used to drive one or more transducers with their outputs directed to reduce noise caused by a rotating device. In some cases, at least one of the noise sources does not include a rotating device. At least one of the noise cancellers can be configured to create a fixed frequency noise reduction signal based on a frequency value received from computer memory.

In another aspect, a system for reducing harmonic noise caused by a plurality of noise sources of a motor vehicle by causing one or more loudspeakers to produce sounds that are at about the same frequencies as the noise and of substantially opposite phase, includes a plurality of noise cancellers, each noise canceller comprising a harmonic sine wave generator that generates an output sine wave having a frequency that corresponds to the noise to be reduced, and an adaptive filter that uses a sine wave to create a noise reduction signal that is used to drive one or more transducers with their outputs directed so as to reduce noise in a vehicle cabin that is caused by the noise sources. There is an overlap detector that compares the frequencies of the noise caused by the plurality of noise sources and, based on the proximity of the frequencies of the noise caused by the plurality of noise sources, alters the operation of one or more of the adaptive filters (e.g., adaptation step size and/or leakage parameter), wherein the overlap detector alters operation of one or more of the adaptive filters by changing the values of one or more variable parameters of an adaptive filter, wherein the variable parameters comprise the adaptation step sizes of the adaptive filters, and the step sizes are decreased when the proximities of the frequencies are close. A computer memory stores relationships between the proximity of the frequencies and the resulting changes in the values of the adaptive filter parameters. The rotating devices may be the vehicle engine and the vehicle propeller shaft.

Embodiments may include one of the above and/or below features, or any combination thereof.

In yet another aspect, a method for operating an active noise reduction system that is adapted to reduce noise caused by a plurality of noise sources, where the active noise reduction system comprises separate adaptive filters associated with each of the noise sources, the adaptive filters having tuning parameters that affect their outputs, the adaptive filters outputting noise reduction signals that are used to drive one or more transducers with their outputs directed to reduce noise caused by the noise sources, includes determining the proximity of the frequencies of the noise caused by the plurality of noise sources and changing the values of one or more variable parameters based on the determined proximity of the frequencies of the harmonic noise caused by the plurality of noise sources.

Embodiments may include one of the above and/or below features, or any combination thereof. The method may further include the step of storing in a computer memory relationships between the proximity of the frequencies and the resulting changes in the values of the adaptive filter parameters. The variable parameters can include the adaptation step sizes of the adaptive filters, and the step sizes may be decreased when the proximities of the frequencies are close. The adaptation step size may be decreased by about one-half when two input signal frequencies are approximately coincident. The values of the variable parameters may be computed and provided to the adaptive filters. The proximity of the frequencies may be determined by an overlap detector that provides control signals to affect the computation of the values of the variable parameters. The transducer outputs may be directed into a cabin of a motor vehicle.

DETAILED DESCRIPTION

Figure 1:
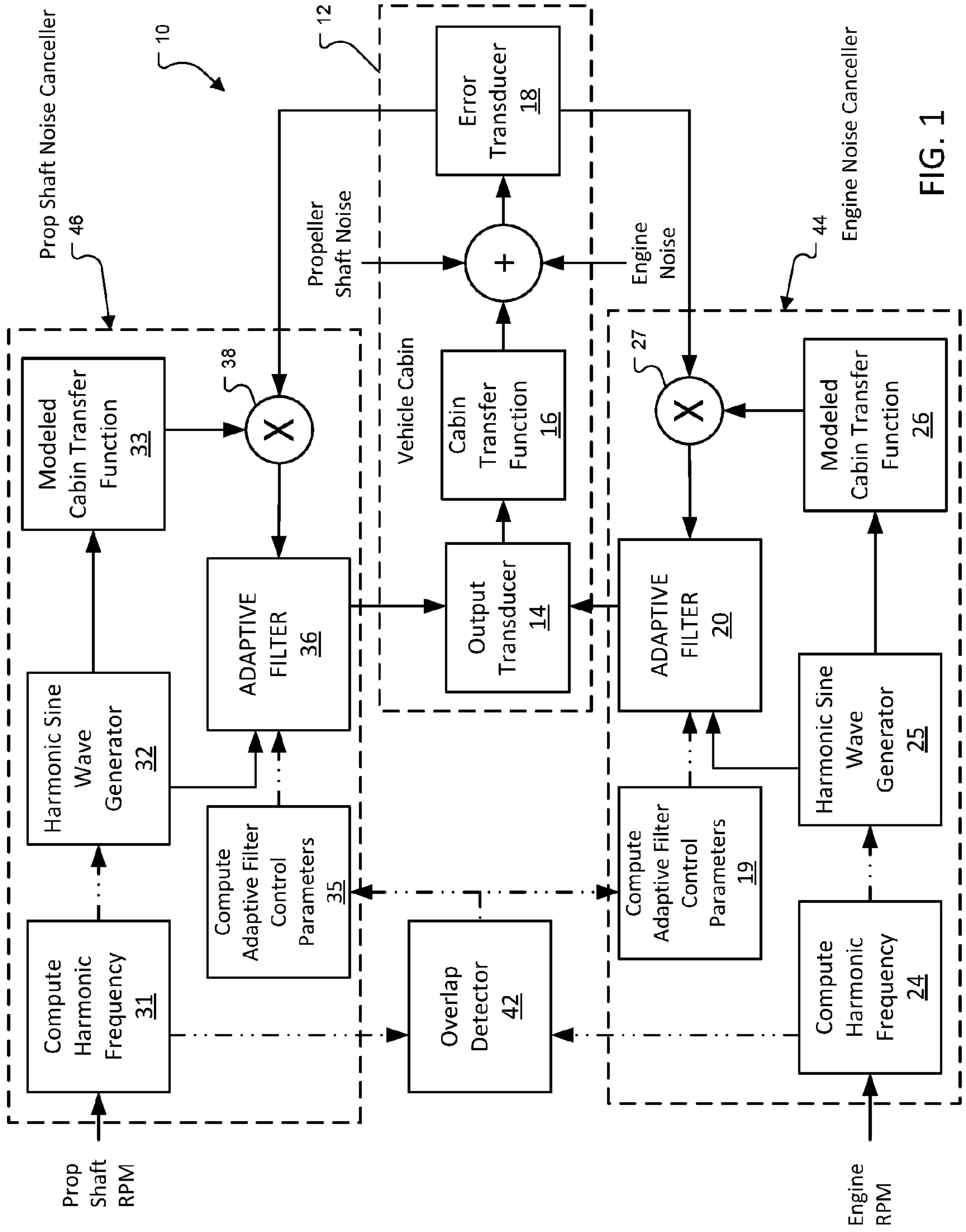
FIG. 1 is a schematic block diagram of a harmonic cancellation system that can be used to accomplish the system, device and method of the present innovation.

Elements of FIG. 1 of the drawings are shown and described as discrete elements in a block diagram. These may be implemented as one or more of analog circuitry or digital circuitry. Alternatively, or additionally, they may be implemented with one or more microprocessors executing software instructions. The software instructions can include digital signal processing instructions. Operations may be performed by analog circuitry or by a microprocessor executing software that performs the equivalent of the analog operation. Signal lines may be implemented as discrete analog or digital signal lines, as a discrete digital signal line with appropriate signal processing that is able to process separate signals, as a multiplexed digital signal bus, and/or as elements of a wireless communication system.

When processes are represented or implied in the block diagram, the steps may be performed by one element or a plurality of elements. The steps may be performed together or at different times. The elements that perform the activities may be physically the same or proximate one another, or may be physically separate. One element may perform the actions of more than one block. Audio signals may be encoded or not, and may be transmitted in either digital or analog form. Conventional audio signal processing equipment and operations are in some cases omitted from the drawing.

FIG. 1 is a simplified schematic diagram of harmonic noise cancellation system 10 that embodies the disclosed innovation. The system 10 is design to cancel harmonic noise from multiple noise sources. In this non-limiting example system 10 is designed to cancel both engine noise and propeller shaft noise in the cabin of a motor vehicle. However, system 10 can be used to reduce harmonic noise emanating from any two or more noise sources (e.g., two or more rotating devices, such as two or more motors). System 10 can also be used to reduce harmonic noise in locations other than motor vehicles and in volumes other than motor vehicle cabins. As one non-limiting example, system 10 could be used to cancel engine harmonics, prop shaft harmonics and harmonics due to the air conditioning compressor in a motor vehicle. In FIG. 1 signal flow is indicated with solid arrows and control signals are indicated by dash/dot lines with arrowheads.

System 10 in this case has two parallel harmonic noise cancellers: engine noise canceller 44 reduces or cancels engine harmonic noise in cabin 12, while prop shaft noise canceller 46 reduces or cancels propeller shaft harmonic noise in cabin 12. Each canceller can be implemented as computer code in the digital signal processor that is used to accomplish the adaptive filter. In this non-limiting example the adaptive algorithm is a filtered x adaptive algorithm. However, this is not a limitation of the innovation as other adaptive algorithms could be used, as would be apparent to those skilled in the technical field.

Each canceller 44 and 46 computes the harmonic frequencies to be cancelled from the input RPM: canceller 44 has harmonic frequency computer 24 that is input with the engine RPM, and canceller 46 has harmonic frequency computer 31 that is input with the prop shaft RPM. Each canceller has a harmonic sine wave generator (25 and 32, respectively) that generates sine waves at the frequencies to be cancelled. Sine wave generators 25 and 32 are input with the computed harmonic frequencies based on the inputs from the noise sources (in this case a pair of rotating devices) that are to be cancelled. Adaptive filters 20 and 36, respectively, supply transducer drive signals to one or more output transducers 14 that have their outputs directed into vehicle cabin 12. The residual noise after the output of the transducers, as modified by the cabin transfer function 16, is combined with the engine noise and propeller shaft noise in the vehicle cabin and is picked up by an input error transducer (e.g., microphone) 18.

Sine wave generator 25 provides to adaptive filter 20 a noise reduction reference signal that includes the harmonics of the engine frequency that are to be cancelled using adaptive filter 20. "Harmonic" as used herein can include half harmonics or quarter harmonics, and for simplicity includes the fundamental frequency. The output of sine wave generator 25, which is referred to as the "x signal," is also provided to modeled cabin transfer function 26, to produce a filtered x signal. The filtered x signal and the microphone output signals are multiplied together 27, and provided as a control input to adaptive filter 20. Similarly, sine wave generator 32 provides to adaptive filter 36 a noise reduction reference signal that includes the harmonics of the propeller shaft frequency that are to be cancelled using adaptive filter 36. The output of sine wave generator 32 is also provided to modeled cabin transfer function 33, to produce a filtered x signal. The filtered x signal and the microphone output signal are multiplied together 38, and provided as a control input to adaptive filter 36. The operation of adaptive feed-forward harmonic noise cancellation systems is well understood by those skilled in the art.

Overlap detector 42 takes in as control signals from frequency computers 24 and 31 the harmonic frequencies that are going to be cancelled, and makes a decision of when the frequencies are close enough to affect the stability margin. If so, it causes the adaptive filters to automatically change the value of one or more variables of the adaptive algorithm. In the present case in which a filtered x adaptive algorithm is used, the variables that are changed can be one or both of the adaptation step size and the leakage parameter. Adaptation step size and leakage in an adaptive algorithm are disclosed in U.S. Pat. Nos. 8,194,873, 8,204,242, 8,355,512, and 8,306,240, the disclosures of which are incorporated herein by reference.

More generally, changes are made by the system to one or more of the filtration algorithms with the aim of maintaining the stability margin so as to keep the performance of the system close to what it would be with a single canceller. A reason that performance can be maintained to an acceptable level when the overlap happens is that multiple cancellers are working at the same frequency region instead of just one. In general, the detector can have multiple degrees of overlap, and for each it can have ability to select from predetermined values of the appropriate adaptive algorithm parameters.

As one non-limiting example: If the prop shaft canceller is set to cancel the first order prop harmonic frequency and the prop RPM is 3000, the first order prop harmonic frequency is 50 Hz (1×3000/60). If the engine canceller is set to cancel the 1.5 order engine harmonic frequency and in the current gear the engine RPM is 2000, the 1.5 order engine frequency would be 50 Hz (1.5×2000/60). In this example the two frequencies to be cancelled are exactly the same, so both adaptive filters 20 and 36 will produce the same cancellation frequency. The degree by which the engine and prop frequencies overlap will vary with the gear ratio, or within the same gear one can have torque convertor slippage which can also cause the frequencies to overlap.

Generally, two cancellers working at the same frequency means that the cancellation is more effective, as the cancellation system's adaptation step size is effectively doubled. However, the larger adaptation step size means that there is less margin for transfer function variation before the system will become unstable and potentially diverge.

The present innovation can account for the increase in cancellation algorithm adaptation step size when the two frequencies being cancelled are coincident or close to each other. In the example described just above, by automatically decreasing the adaptation step size by 0.5 the original single canceller performance is maintained and so the original stability margin is regained.

It may be advantageous to allow a margin in the estimated transfer function, as in the real world each production car will have variation from the one that was used to do the original tuning due to component tolerances, temperature variation, passenger/cabin loading etc. In practice the reduction in adaptation step size may not be exactly 0.5. More specifically, one or more adjustable filter parameters can be empirically chosen so as to maintain optimum cancellation and stability margin. These parameters can be empirically determined at time of tuning to accomplish the best tradeoff to handle the overlapping condition. Other conditions such as noise source location will determine what the optimum would be. Also, the cancellers can have the capability to adjust other adaptive algorithm parameters, such as leakage, as necessary to maintain the right balance of performance and stability margin. In cases in which an algorithm other than the filtered x adaptive algorithm is used in the adaptive filters, other variables that are mutually effective can be chosen to be modified in a similar manner with the goal of maintaining the original single canceller performance and thus regain the original stability margin.

The above example was for an idealized case where there is perfect overlap. More generally, stability margin can be lost when the frequencies are close. So, overlap detector 42 can be set for the proximity of the two (or more) frequencies, multiple frequencies being another tunable parameter that is determined empirically at time of tuning. Likewise, the system can account for more than one band of overlap. The system can be expanded to multiple levels of overlap, with each having independent changes to the selected filter parameters, the values typically being determined empirically a priori and then stored in computer memory and retrieved during operation of the system based on the proximity of the two frequencies. More generally in the example described herein, the change in adaptation step size can be set as a function of the proximity of the two frequencies. When there are more than two frequencies being cancelled, a pair-wise comparison of all the frequencies would be used.

One result of the subject innovation is that the harmonic cancellation systems are less likely to diverge. Another benefit is that detectable noise artifacts due to system instability are minimized.

Figure 2:
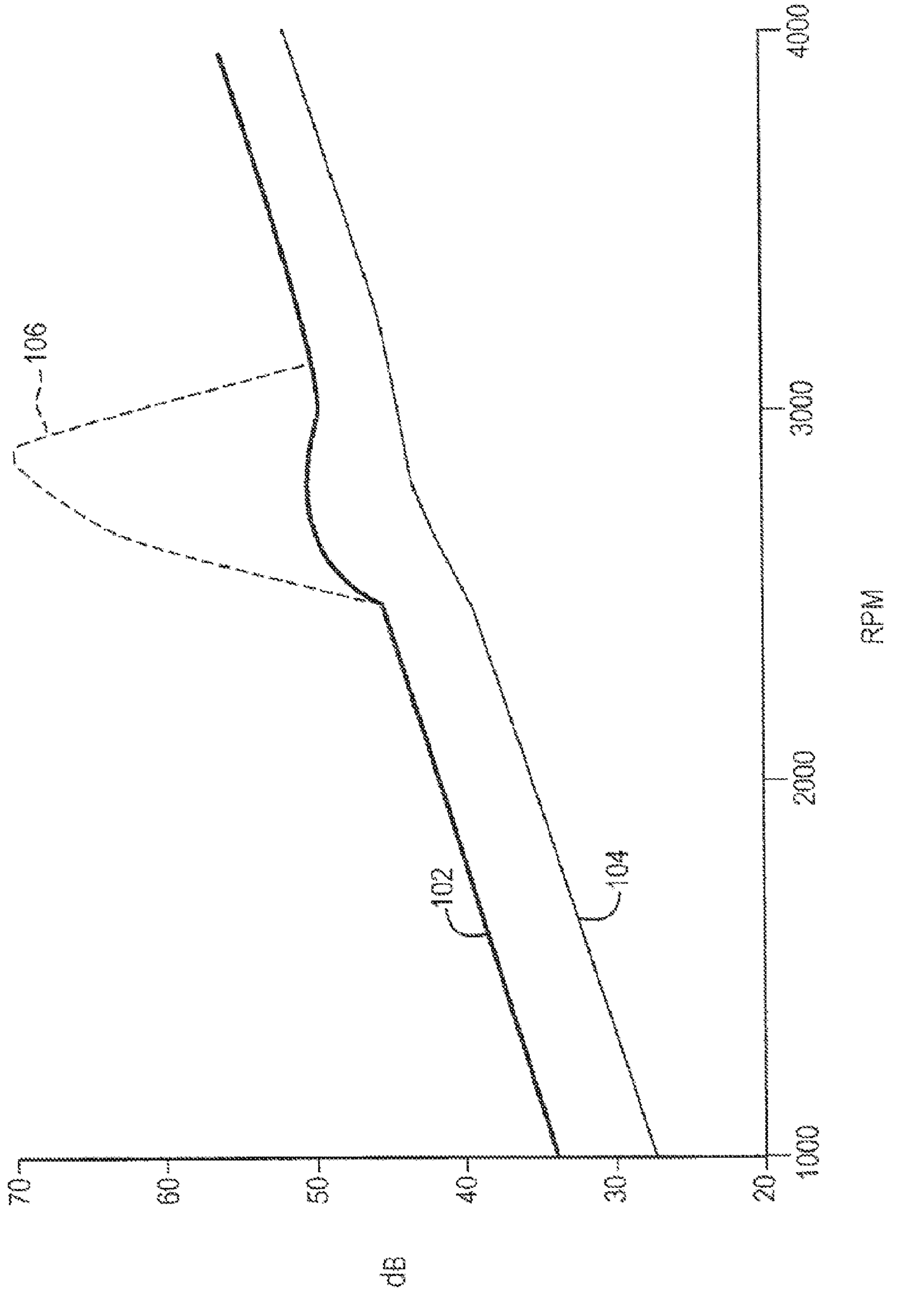
FIG. 2 illustrates noise in a vehicle cabin.

An idealized, non-limiting example of a manner in which the innovation can operate is illustrated with reference to FIG. 2, which illustrates an example of algorithm adjustment due to overlapping cancellation frequencies in a noise cancellation system such as that shown in FIG. 1 that is designed and operated to cancel engine harmonics and propeller shaft harmonics in a motor vehicle cabin. The engine RPM (input from the vehicle's tachometer) is set out along the x axis, with the cabin noise sound pressure level (SPL) on the y axis, in dB. Curve 102 illustrates the baseline noise, and curve 104 illustrates the reduction in noise when the cabin engine and prop shaft harmonic noise cancellation system is turned on, with the two cancellers operating at the same frequency. Curve 104 illustrates a reduction of about 10 dB across most of the normal automobile operating range.

Curve 106 (in dashed line) illustrates an excursion in the sound when the engine and prop shaft noise cancellation systems are both on and there is a change in cabin transfer function that results in the creation of noise artifacts that increase the sound levels quite dramatically around the frequency corresponding to around 3000 RPM. The system disclosed herein would be enabled to alter the values of one or more parameters of the adaptive filter algorithm to bring the operation back closer to curve 104, where it would be if only one canceller was being used.

The above was described relative to noise cancellation in a vehicle cabin. However, the disclosure applies as well to noise cancellation in other vehicle locations. One additional example is that the system can be designed to cancel noise in a muffler assembly. Such noise may be engine harmonic noise but may also be other engine-operation related noise and/or noise caused by another noise source, such as another rotating device, in the vehicle.

Although an implementation of a harmonic noise cancellation system has been described which can be used for noise emanating from two or more rotating devices, in some instances, one more sources of noise may be something other than a rotating device. For example, the noise sources could include resonance in the vehicle cabin resulting from vibration of cabin components, such as interior trim or the vehicle headliner. Another example of a non-rotating noise source could be noise resulting from air/wind passing through the vehicle cabin (e.g., via a vent or open window) or through the engine compartment. In such cases, a sensor (such as a microphone or an accelerometer) could be used to detect the noise and output of the sensor could be sent to an associated frequency computer (such as frequency computer 31 in FIG. 1), which would then provide the frequency to be canceled to a sine wave generator (such as item 32, FIG. 1) and so on. The system may operate in the same manner as discussed above with reference to FIG. 1, the only difference being the source of the harmonic noise.

In some implementations, the harmonic noise cancellation system may alternatively or additionally be provided with a fixed frequency noise canceller for cancelling noise at a fixed frequency. For example, the harmonic noise cancellation system may include a fixed frequency noise canceller for cancelling harmonic noise at 200 Hz. In which case, the frequency to be cancelled could be known a priori, thus eliminating the need for a frequency computer.

Figure 3:
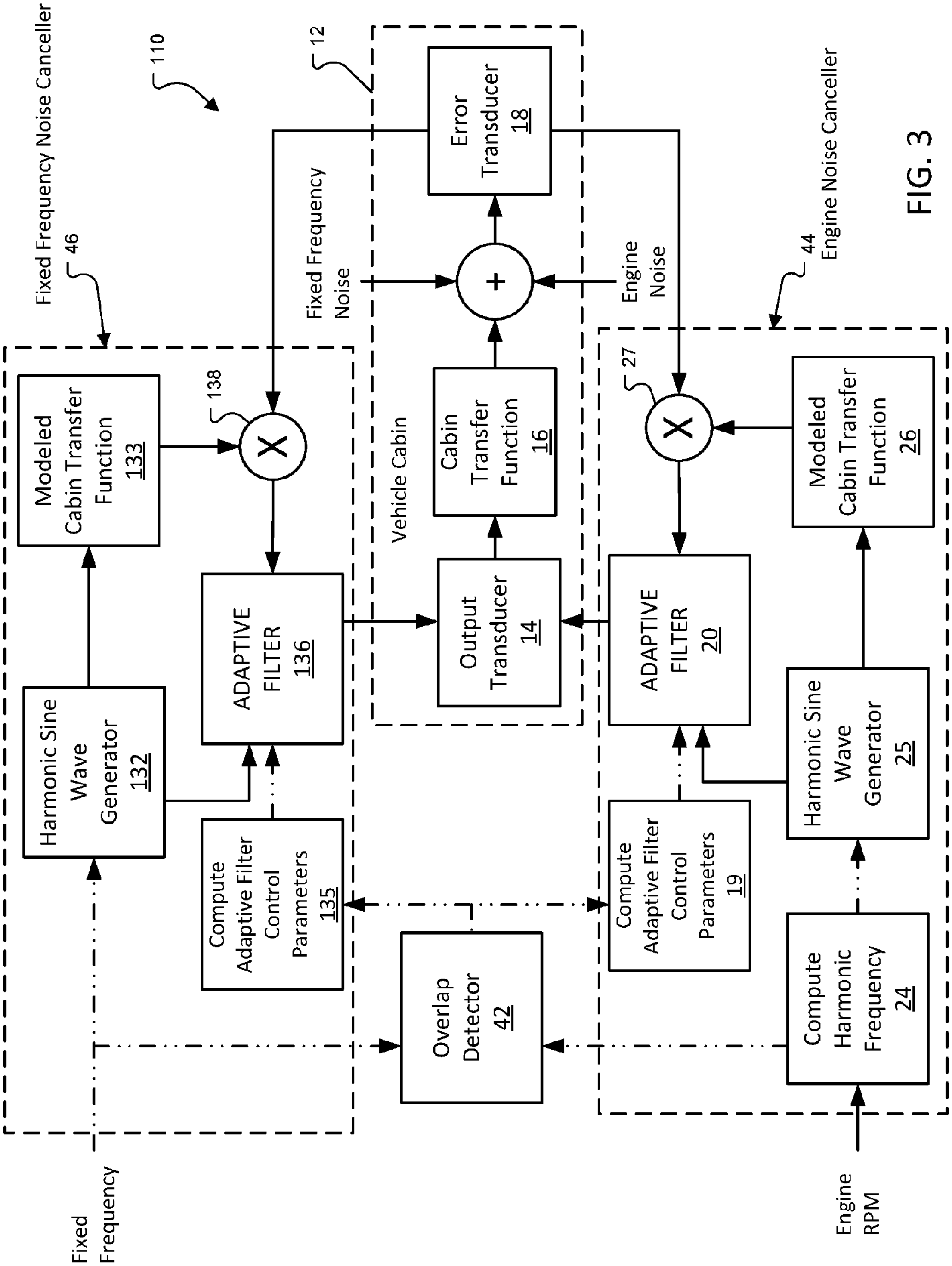
FIG. 3 is a schematic block diagram of a harmonic cancellation system that can be used to accomplish fixed frequency noise cancellation with the system, device and method of the present innovation.

For example, FIG. 3 is a simplified schematic diagram of harmonic noise cancellation system 110 that is designed to cancel noise from multiple noise sources. Like reference numbers in FIG. 3 correspond to like elements in FIG. 1. In this non-limiting example system 110 is designed to cancel both engine noise and a fixed frequency noise (e.g., 200 Hz) in the cabin of a motor vehicle. Such fixed frequency noise may emanate from and/or correspond to cabin resonances.

In FIG. 3, signal flow is indicated with solid arrows and control signals are indicated by dash/dot lines with arrowheads. System 110 in this case has two parallel harmonic noise cancellers: engine noise canceller 44 reduces or cancels engine harmonic noise in cabin 12, while fixed frequency noise canceller 146 reduces or cancels fixed frequency noise (e.g., 200 Hz) in cabin 12. Each canceller can be implemented as computer code in the digital signal processor that is used to accomplish the adaptive filter. In this non-limiting example the adaptive algorithm is a filtered x adaptive algorithm. However, this is not a limitation of the innovation as other adaptive algorithms could be used, as would be apparent to those skilled in the technical field.

In FIG. 3, canceller 44 again has harmonic frequency computer 24 that is input with the engine RPM; however, in this case, canceller 146 does not include, and has no need for, a harmonic frequency computer since the noise that it is cancelling pertains to a fixed frequency that is known a priori. Each canceller has a harmonic sine wave generator (25 and 132, respectively) that generates sine waves at the frequencies to be cancelled. In that regard, sine wave generator 132 generates a sine wave at the fixed frequency of interest based on the information received from computer memory. Sine wave generator 25 is input with the computed harmonic frequency from harmonic frequency computer 24, and sine wave generator is input with the fixed frequency to be cancelled, which may be retrieved from computer memory. For example, the fixed frequency may be a value stored in computer memory during system tuning. Adaptive filters 20 and 136, respectively, supply transducer drive signals to one or more output transducers 14 that have their outputs directed into vehicle cabin 12. The residual noise after the output of the transducers, as modified by the cabin transfer function 16, is combined with the engine noise and the fixed frequency noise in the vehicle cabin and is picked up by an input error transducer (e.g., microphone) 18.

Sine wave generator 25 provides to adaptive filter 20 a noise reduction reference signal that includes the harmonics of the engine frequency that are to be cancelled using adaptive filter 20. "Harmonics" as used herein can include half harmonics or quarter harmonics, and for simplicity includes the fundamental frequency. The output of sine wave generator 25, which is referred to as the "x signal," is also provided to modeled cabin transfer function 26, to produce a filtered x signal. The filtered x signal and the microphone output signals are multiplied together 27, and provided as a control input to adaptive filter 20. Similarly, sine wave generator 32 provides to adaptive filter 36 a noise reduction reference signal that includes the harmonics of the propeller shaft frequency that are to be cancelled using adaptive filter 36. The output of sine wave generator 132 is also provided to modeled cabin transfer function 133, to produce a filtered x signal. The filtered x signal and the microphone output signal are multiplied together 138, and provided as a control input to adaptive filter 136.

Overlap detector 42 receives the computed harmonic frequency from harmonic frequency computer 24, and the fixed frequency (e.g., from computer memory) to be cancelled, and makes a decision of when the frequencies are close enough to affect the stability margin. If so, it causes the adaptive filters to automatically change the value of one or more variables of the adaptive algorithm, such as discussed above with reference to FIG. 1.

Embodiments of the devices, systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMS, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component.

Such computer system and/or software components are therefore enabled by describing their corresponding steps or elements (that is, their functionality), and are within the scope of the disclosure.

The various features of the disclosure could be enabled in different manners than those described herein, and could be combined in manners other than those described herein. A number of implementations have been described. Nevertheless, it will be understood that additional modifications may be made without departing from the scope of the inventive concepts described herein, and, accordingly, other embodiments are within the scope of the following claims.

What is claimed is:

1. A system for reducing harmonic noise caused by a plurality of noise sources by causing one or more loudspeakers to produce sounds that are at about the same frequencies as the noise and of substantially opposite phases, the system comprising:

a plurality of noise cancellers including a fixed frequency noise canceller and an engine noise canceller, each noise canceller comprising a harmonic sine wave generator that generates an output sine wave having a frequency that corresponds to the noise to be reduced, and an adaptive filter that uses a sine wave to create a noise reduction signal that is used to drive one or more transducers with their output directed to reduce noise caused by the noise sources; and an overlap detector that compares the frequencies of the noise caused by the plurality of noise sources, and, based on the proximity of the frequencies, alters the operation of one or more of the adaptive filters.

2. The system of claim 1, wherein the overlap detector alters the operation of one or more of the adaptive filters by changing the values of one or more variable parameters of an adaptive filter.

3. The system of claim 2, wherein the variable parameters comprise adaptation step sizes of the adaptive filters, and the step sizes are decreased when the proximities of the frequencies are close.

4. The system of claim 3, wherein the adaptation step size is decreased by about one-half when two input signal frequencies are approximately coincident.

5. The system of claim 2, further comprising a computer memory that stores relationships between the proximity of the frequencies and the resulting changes in the values of the adaptive filter parameters.

6. The system of claim 2, wherein the one or more variable parameters comprise a leakage parameter.

7. The system of claim 1, wherein the transducer outputs are directed into a cabin of a motor vehicle.

8. The system of claim 1, wherein at least one of the noise sources corresponds to resonance in a cabin of a motor vehicle resulting from vibration of one or more cabin components, the resonance being at a fixed frequency.

9. The system of claim 1, wherein the fixed frequency noise canceller is configured to generate a fixed frequency noise reduction signal based on a frequency value received from computer memory.

10. A method for operating an active noise reduction system that is adapted to reduce harmonic noise caused by a plurality of noise sources, wherein the active noise reduction system comprises separate adaptive filters associated with each of the noise sources, the adaptive filters having tuning parameters that affect their outputs, the adaptive filters outputting noise reduction signals that are used to drive one or more transducers with their outputs directed to reduce noise caused by the noise sources, the method comprising:

generating a plurality of sine waves at frequencies of the harmonic noises to be reduced, the plurality of sine waves including a sine wave at a frequency that corresponds to a harmonic noise caused by a fixed frequency noise source;

determining the proximity of the frequencies; and changing the values of one or more variable parameters based on the determined proximity of the frequencies.

11. The method of claim 10, further comprising storing in a computer memory relationships between the proximity of the frequencies and the resulting changes in the values of the adaptive filter parameters.

12. The method of claim 10, wherein the variable parameters comprise the adaptation step sizes of the adaptive filters, and the step sizes are decreased when the proximities of the frequencies are close.

13. The method of claim 12, wherein the adaptation steps size is decreased by about one-half when two frequencies are approximately coincident.

14. The method of claim 10, wherein the variable parameters comprise a leakage parameter.

15. The method of claim 10, wherein the values of the variable parameters are computed and provided to the adaptive filters.

16. The method of claim 15, wherein the proximity of the frequencies is determined by an overlap detector that provides control signals to affect the computation of the values of the variable parameters.

17. The method of claim 10, wherein the transducer outputs are directed into a cabin of a motor vehicle.

18. The method of claim 10, wherein the fixed frequency noise source corresponds to resonance in a cabin of a motor vehicle resulting from vibration of one or more cabin components, the resonance being at a fixed frequency.

* * * * *